United States Patent [19]
Carpentier et al.

[11] 4,106,129
[45] Aug. 15, 1978

[54] SUPPORTED BIOPROSTHETIC HEART VALVE WITH COMPLIANT ORIFICE RING

[75] Inventors: Alain F. Carpentier, Paris, France; Ernest Lane, Huntington Beach, Calif.

[73] Assignee: American Hospital Supply Corporation, Evanston, Ill.

[21] Appl. No.: 827,961

[22] Filed: Aug. 26, 1977

Related U.S. Application Data

[63] Continuation of Ser. No. 647,900, Jan. 9, 1976, abandoned.

[51] Int. Cl.² .............................................. A61F 1/22
[52] U.S. Cl. ......................................................... 3/1.5
[58] Field of Search ......................................... 3/1.5, 1

[56] References Cited

U.S. PATENT DOCUMENTS 3,755,823 9/1973 Hancock .................................. 3/1.5

FOREIGN PATENT DOCUMENTS 158,988 5/1964 U.S.S.R. ........................................ 3/1.5

OTHER PUBLICATIONS

"Clinical Experience with Supported Homograft Heart Valve for Mitral and Aortic Valve Replacement", by S. Sugie et al., The Journal of Thoracic & Cardiovascular Surgery, vol. 57, No. 4, Apr. 1969, pp. 455–463.

"Fixation of Aortic Valve Homografts with Metal Rings", by A. S. Geha et al., The Journal of Thoracic & Cardiovascular Surgery, vol. 54, No. 5, Nov. 1967, pp. 605–615 & 628–629.

Primary Examiner—Ronald L. Frinks
Attorney, Agent, or Firm—Tilton, Fallon, Lungmus & Chestnut

[57] ABSTRACT

A supported bioprosthetic heart valve in which the supporting stent is capable of annular deformation and also of limited perimetric expansion and contraction during heart operation. The stent includes a wire frame composed of a single flexible wire preformed to define inverted U-shaped commissure supports merging smoothly with arcuate portions connecting such supports.

29 Claims, 10 Drawing Figures

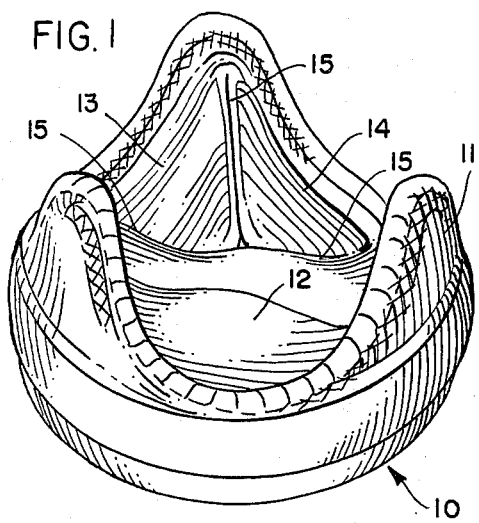
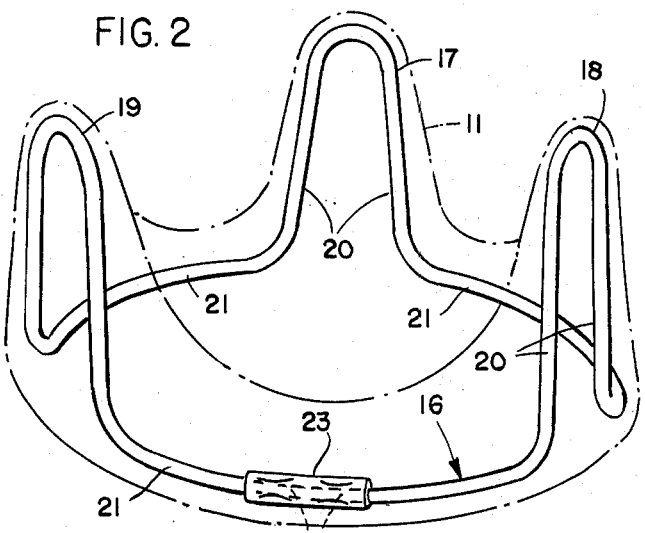
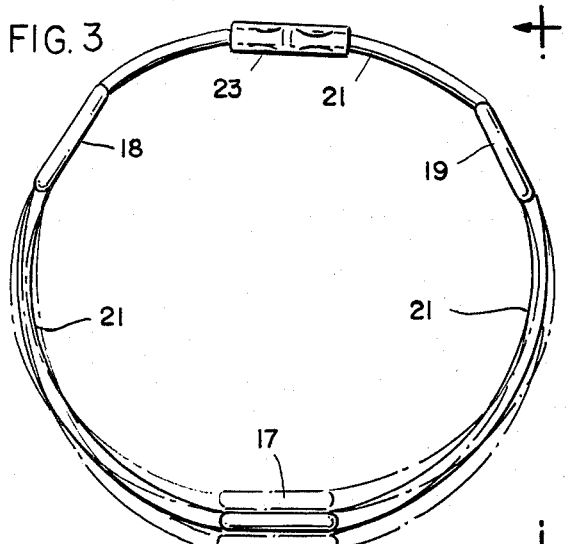
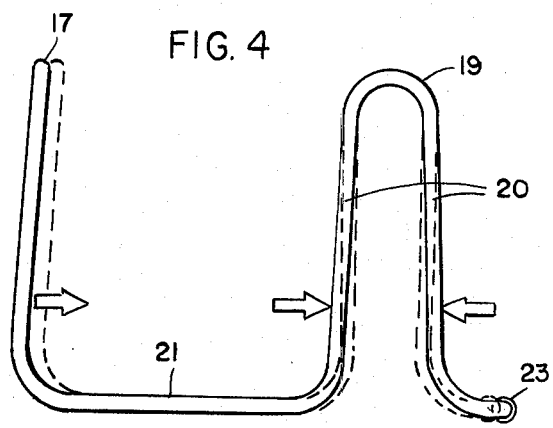
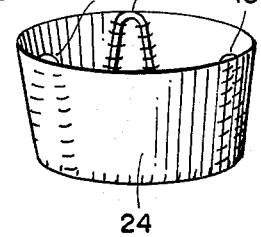
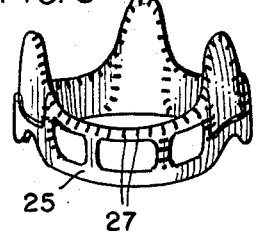
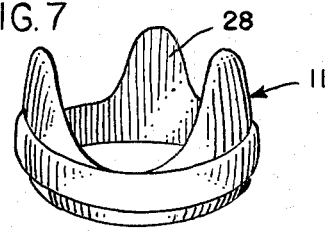
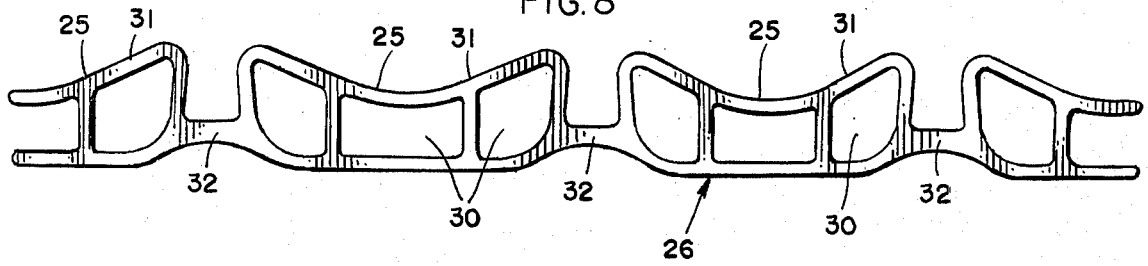

SUPPORTED BIOPROSTHETIC HEART VALVE WITH COMPLIANT ORIFICE RING

RELATED APPLICATION

This application is a continuation of copending application Ser. No. 647,900, filed Jan. 9, 1976, now abandoned.

BACKGROUND

Stented bioprosthetic valves — that is, supported valvular grafts which may be either xenografts (heterografts) or allografts (homografts) — are believed to have important clinical advantages over mechanical non-tissue prosthetic valves. Reports on the use of xenograft valves indicate that the risks of thromboembolism are lower, the need for long-term anticoagulation is minimized, and the nature of ocassional valve failure is progressive, thereby permitting elective reoperation under optimal conditions. Carpentier et al, J. Thorac. Cardiovasc. Surg. 68:771 (1974); Zuhdi et al, Ann. Thorac. Surg. 17:479 (1974); Horowitz et al, J. Thorac. Cardiovasc. Surg. 67:885 (1974).

In general, such grafts have been mounted on supporting frames which provide rigid orifice rings (see U.S. Pat. Nos. 3,570,014, 3,755,823; Weldon et al J. Surg. Research 6:548 (1966)), even though some stents have included struts capable of flexing inwardly to a limited extent, thereby reducing stresses imposed on the grafts during valve operation and decreasing possible erosion of surrounding tissues of the patient (see Sugie et al, J. Thorac. Cardiovasc. Surg. 57:455 (1969); Hardy, Human Organ Support and Replacement, 338 et. seq. (Thomas, 1971); U.S. Pat. No. 3,755,823). Despite encouraging results in the use of stented valvular grafts, and the significant advantages of bioprosthetic heart valves in contrast to totally artificial prosthetic valves, there is a continuing need for improvement, particularly with regard to the long range durability and reliability of the supported valvular grafts.

SUMMARY

The present invention is concerned with an improved stent for a bioprosthetic (xenograft or allograft) heart valve which is flexible and, in particular, is capable of yielding to a limited extent in response to forces which tend to alter the configuration and circumference of the orifice ring. Such flexibility and deformability allows the leaflets to close with a sliding type of closure at their free margins which is similar to that observed physiologically, and are believed to be significant in improving long range reliability of the valves.

Conformability of the orifice-defining portion of th prosthetic valve is achieved primarily by utilizing a flexible supporting frame consisting essentially of a single piece or stretch of preformed spring wire. The wire frame is formed to define a triad of axially-projecting circumferentially-spaced commissure supports. Each commissure support has a generally inverted U-shaped configuration with its wire legs merging smoothly at their spaced lower ends with arcuate connecting portions of the wire frame which extend circumferentially between the legs of adjacent commissure supports. Each arcuate connecting portion is capable of being flexed into a condition of greater or lesser curvature, thereby providing limited deformability of the frame's orifice-defining elements. Furthermore, each of the three arcuate connecting portions may be moved to a slight but definite extent independently of the other such portions. Since the wire frame of each commissure support is of inverted U-shaped configuration with the lower ends of the legs thereof normally disposed in spaced-apart relation, the arcuate portions with which the lower ends of the legs smoothly merge may be urged circumferentially towards and away from each other in response to forces occurring during operation of the heart. The result is a flexible frame which is capable of limited changes in dimension and configuration during heart operation.

Insert elements extend between the circumferentially-spaced commissure supports, each of the inserts having an arcuate upper margin sloping upwardly at its ends to merge smoothly with the contour of the commissure supports. The insert elements may be formed integrally as portions of a web of flexible perforated plastic material circumscribing the wire frame. An outer covering of porous fabric extends about the frame and insert elements to provide means for suturing the valve in place and for accommodating tissue ingrowth. A suitable annular cushioning element is also enclosed within the outer covering to promote coaption, the configuration of the cushioning element depending upon the intended use of the valve in a mitral, aortic, or tricuspid position.

DRAWINGS

FIG. 1 is a perspective view of a bioprosthetic heart valve embodying the present invention.

FIG. 2 is a perspective view illustrating the supporting wire frame for the valve.

FIG. 3 is a top plan view of the wire frame.

FIG. 4 is a side elevational view of the frame.

FIGS 5–7 are reduced perspective views illustrating steps in the fabrication of the stent.

FIG. 8 is a plan view in reduced scale showing the interconnected insert elements of the valve.

DESCRIPTION

Figure 9:
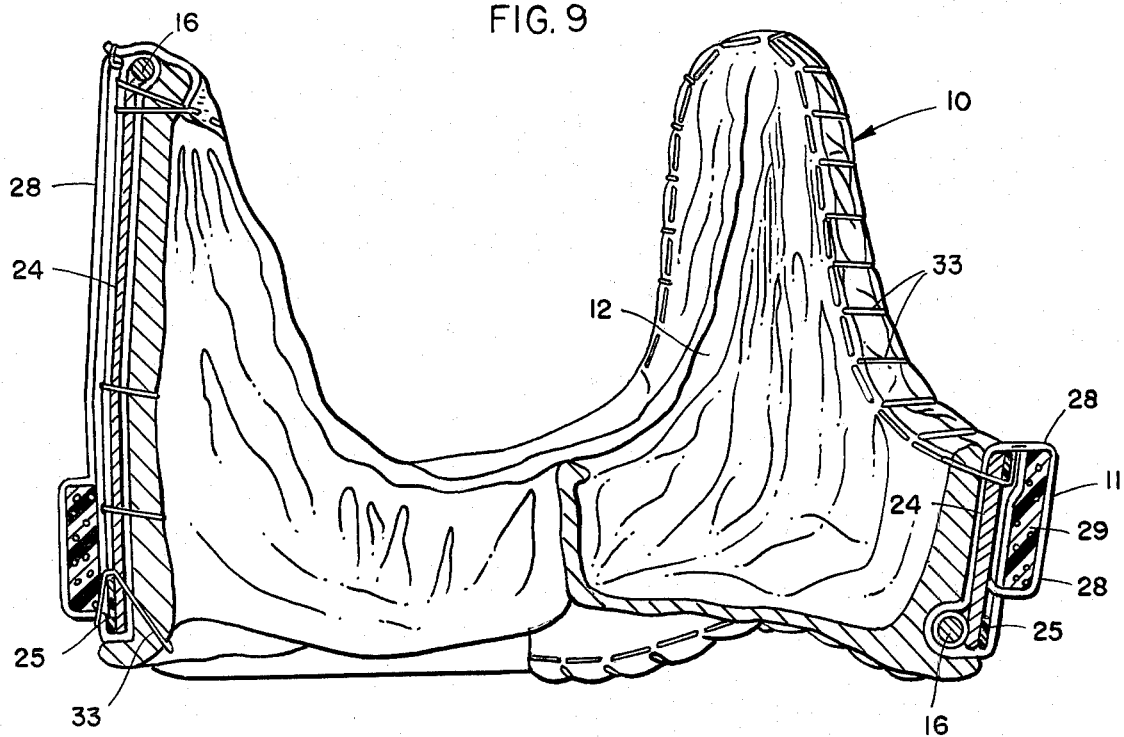
FIG. 9 is an enlarged vertical sectional view of a complete bioprosthetic aortic valve embodying the invention.

Referring to FIG. 1, the numeral 10 generally designates a bioprosthetic valve adapted for implantation in the aortic position. Whether the valve is adapted for replacement of a natural aortic valve, or of a mitral or tricuspid valve, depends largely on the size of the valve and the construction of its suturing cuff or ring. As far as this invention is concerned, all three types of valves have the same essential features and, therefore, an aortic valve has been selected only for purposes of illustration.

Valve 10 comprises a stent 11 and a valvular graft 12. Typically, the graft would be a preserved porcine xenograft; however, the stent may be used to support grafts from other species and, if desired, may provide support for an allograft (homograft).

Graft 12 has three leaflets 13–15 meeting along commissures 15. The treatment and preservation of the graft are now well known, as disclosed in Carpentier et al, J. Thorac. Cardiovasc. Surg. 68:771 (1974) and the references cited therein, and need not be discussed in detail here.

Stent 11 consists essentially of a flexible wire frame 16 which is gusseted, padded, and covered with a porous biocompatible fabric so that the completed valve may be sutured in position within a human heart and will allow the ingrowth of tissue into the fabric covering. Frame 16 is generally annular in configuration and consists essentially of a single piece of spring wire formed to define a triad of axially-projecting and circumferentially-spaced commissure supports 17-19. As shown in FIG. 2, each commissure support is generally of inverted U-shaped configuration, having wire legs 20 merging smoothly at their spaced lower ends with arcuate connecting portions 21. The arcuate connecting portions extend circumferentially and join the adjacent legs of adjoining commissure supports.

The wire from which the frame is formed has its ends 22 joined together along one of the arcuate connecting portions 21 by means of a crimped sleeve or coupling 23. Both the location and the manner of connection are important if long term durability of the stent is to be achieved. The mid zone of an arcuate connecting portion 21 has been found to be an area of relatively low stress and the use of a coupling sleeve or tube, crimped to each of the end portions, avoids the problems of material degradation, and surprisingly rapid fatigue failure, associated with a welded connection.

The wire is circular in cross section and, except for sleeve 23, is of substantially uniform diameter throughout its entire extent. Each inverted U-shaped commissure support has a rounded or smoothly-curved upper end. Similarly, the lower ends of legs 20 of the commissure supports curve outwardly to merge smoothly, not abruptly, with the connecting portions 21. As shown in FIGS. 2 and 4, the legs 20 of each U-shaped support are straight and generally parallel along substantial portions of their length.

The frame or wireform may be formed of any spring material which is non-corrosive, fatigue resistant, and biocompatible. A particularly effective material is a steel marketed under the name Elgiloy by Elgiloy Company, Elgin, Ill., although other stainless steels or alloys having similar properties might be used.

It will be observed that the arcuate connecting portions 21 in the aggregate define the outline for the orifice ring of the valve. Also, as clearly depicted in FIGS. 2 and 4, each of the connecting portions or segments 21 has a major part of its length extending along a plane normal to the axis of the valve. Since the connecting portions or segments are interrupted by commissure supports 17-19, and since the lower ends of each pair of legs 20 are spaced apart, inward flexure of the legs, as depicted in FIG. 4, reduces the spacing between adjacent connecting segments 21 and thereby decreases the effective perimeter of the orifice ring. Thus, frame 16 is capable of limited contraction and expansion as the spring legs of the commissure supports flex inwardly and outwardly.

In addition, the connecting portions or segments 21 are themselves capable of limited flexure. In particular, the curvature of each arcuate segment 21 may increase or decrease slightly. Such flexure permits slight but significant changes in the positions of the commissure supports relative to each other and to the axis of the valve, as indicated in broken lines in FIG. 3. In general, the configuration of the orifice ring may be altered in response to forces exerted during each beat of the heart in which the bioprosthetic valve is implanted. The result is a valve stent of limited deformability, one which has the capability of expanding and contracting to a slight but definite extent, during heart operation. Such compliance is believed important not only in achieving improved durability or long-term reliability of the xenograft or allograft, but also in allowing the leaflets to close with a sliding type of closure at their free margins which is more similar to that observed physiologically.

The wireform is covered with a padded, gusseted and porous covering to facilitate attachment, tissue invasion, and encapsulation. FIGS. 5-7 illustrate steps in the fabrication of the final stent. A sleeve 24 of porous biocompatible cloth is fitted about the wireform and is loosely stitched thereto as indicated in FIG. 5. Thereafter, insert elements which, in the illustration given, are portions 25 of a plastic web 26, are positioned outside of the sleeve 24 between each of the commissure supports 17-19. The sleeve is trimmed and secured by stitching 27 to the margins of the insert elements. A covering of porous biocompatible cloth 28 is then fitted about the stent, completely enclosing the wireform and inserts as shown in FIG. 7. While the cloth may be folded upon itself about the outer periphery of the stent to form a padded suturing rim, it is preferred that such padding be achieved by enclosing an annulus of resilient foam or sponge rubber 29 (FIG. 9) within the cloth covering 28. The construction and operation of such padded suturing rims is well known in prosthetic valve construction, being disclosed, for example, in U.S. Pat. Nos. 3,099,016, 3,365,728, and 3,371,352.

The cloth layers 24 and 28 may be formed of porous woven or knitted Teflon, although other materials such as Dacron might be used. The insert elements 25 may be formed from a sheet or sheets of polyglycol terephthalate (Mylar) although other inert biocompatible materials such as polypropylene might be utilized.

The insert elements 25 serve as gussets for increasing the axial dimensions of the stent in the zones between the commissure supports 17-19 and for providing attachment for cloth 24 and for the xenograft or allograft 12. Each insert element 25 of the connected series illustrated in FIG. 8 is provided with apertures 30 through which stitching 27 is extended during fabrication of the stent. The upper margin 31 of each insert is arcuate or scallop-shaped to define a smooth transition from the outline of the upper portion of each commissure support.

The three insert elements 25 might be separate components individually secured to the cloth-covered wireform but, to facilitate fabrication, it is preferred to form the elements as a continuous web 26, the successive elements being joined by connecting portions 32 (FIG. 8). It is to be understood that neither the connecting portions 32 nor the other portions of the insert elements significantly alter the flexing characteristics of the wireform as previously described.

Figure 10:
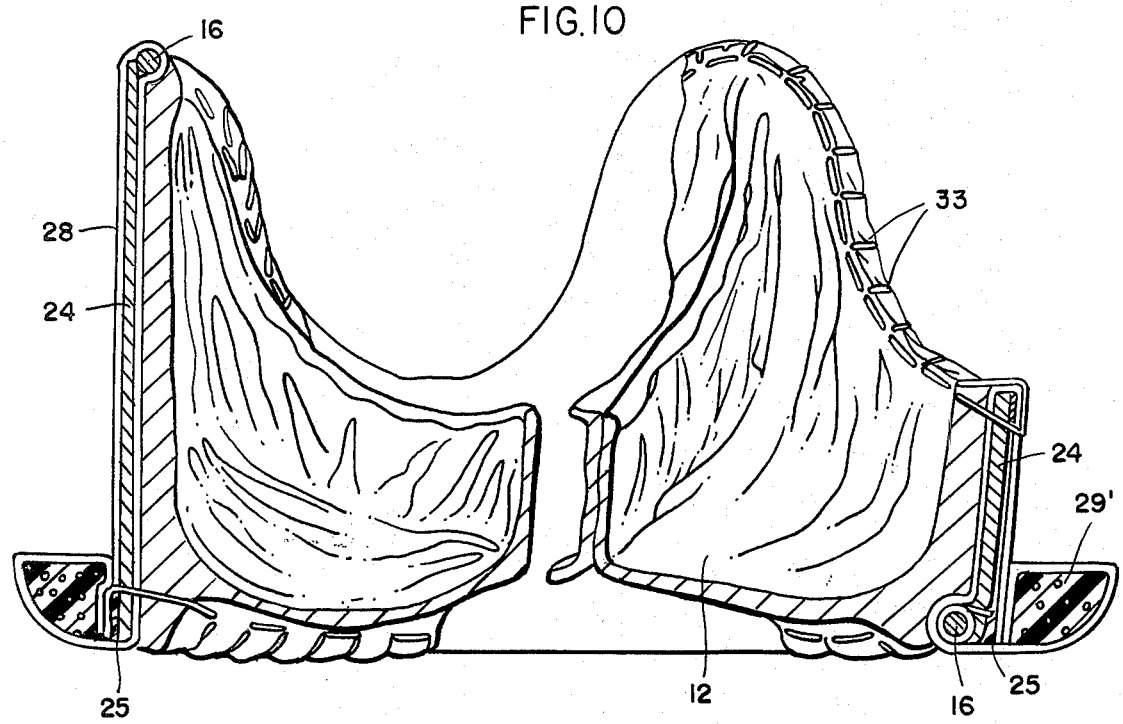
FIG. 10 is an enlarged sectional view of a mitral valve embodying the invention.

FIG. 9 illustrates details of the completed valve with the graft secured to the stent by sutures 33. The configuration and location of foam insert 29 are particularly suited for use of the valve as an aortic valve replacement. The valve illustrated in FIG. 10 is adapted for mitral replacement and, accordingly, has somewhat different proportions. The annular foam insert 29' is positioned and shaped to engage the mitral annulus, all as well known in the art. Except for the obvious differences shown in FIGS. 9 and 10, differences occasioned by the anatomical characteristics of those portions of the human heart to which the respective valves are to be secured, the valves depicted in these figures are essentially the same, both utilizing wireforms as generally shown in FIGS. 2-4.

While in the foregoing we have disclosed embodiments of the invention in considerable detail for purposes of illustration, it will be understood by those skilled in the art that many of these details may be varied without departing from the spirit and scope of the invention.

We claim:

1. A supported bioprosthetic heart valve comprising a stent and a valvular graft secured thereto, said stent having an annular frame consisting essentially of a single piece of preformed spring wire, said wire frame being formed to define a triad of axially-projecting circumferentially-spaced commissure supports, each commissure support being of inverted U-shaped configuration having wire legs spaced substantially apart and merging smoothly at their lower ends with arcuate connecting portions extending circumferentially between and joining the legs of adjacent commissure supports, each of said arcuate connecting portions having a major part of the length thereof extending along a plane normal to the axis of said valve.

2. The valve of claim 1 in which each of the commissure supports of said frame is rounded at its upper end and the wire legs thereof are generally parallel along substantial portions of their length.

3. A supported bioprosthetic heart valve comprising a stent and a valvular graft secured thereto, said stent having an annular frame consisting essentially of a single piece of preformed spring wire, said wire frame being formed to define a triad of axially-projecting circumferentially-spaced commissure supports, each commissure support being of inverted U-shaped configuration having wire legs meging smoothly at their lower ends with arcuate connecting portions extending circumferentially between and joining the legs of adjacent commissure supports, said stent including insert elements extending between said commissure supports and having upper margins disposed above said connecting portions of said frame.

4. The valve of claim 3 in which said insert elements are provided with a plurality of apertures.

5. The valve of claim 3 in which said insert elements are integral portions of a web of flexible perforated plastic material circumscribing said frame.

6. The valve of claim 5 in which said web is provided with scalloped upper edge portions between said commissure supports.

7. The valve of claim 3 in which said graft is connected by lines of stitching to said frame and said insert elements.

8. The valve of claim 3 in which said upper margins of said insert elements are arcuate.

9. The valve of claim 3 in which said insert elements extend from the upper margins thereof to said connecting portions of said frame.

10. The valve of claim 3 in which said stent includes a sleeve of cloth between said frame and said insert elements, said cloth sleeve being stitched to said frame and said insert elements being stitched to said cloth sleeve.

11. The valve of claim 3 in which said insert elements are formed integrally from a sheet of flexible perforated polyglycol terephthalate.

12. The valve of claim 5 in which said web is formed from a material of sufficient flexibility that it does not significantly alter the ability of the spaced wire legs of each commissure support to flex towards and away from each other.

13. The valve of claim 5 in which said web is formed from polyglycol terephthalate.

14. A supported bioprosthetic heart valve comprising a stent and a valvular graft secured thereto, said stent having an annular frame consisting essentially of a single piece of preformed spring wire, said wire frame being formed to define a triad of axially-projecting circumferentially-spaced commissure supports, each commissure support being of inverted U-shaped configuration having wire legs merging smoothly at their lower ends with arcuate connecting portions extending circumferentially between and joining the legs of adjacent commissure supports, said wire of said frame having end portions joined together at a point intermediate the length of one of said arcuate connecting portions, said end portion being joined together by a tubular sleeve extending over and joined to both of said end portions.

15. The valve of claim 14 in which said sleeve is crimped tightly about both of said end portions.

16. A flexible stent for supporting a valvular graft, said stent having an annular frame formed of spring wire, said frame including a triad of axially-projecting circumferentially-spaced commissure supports, each commissure support being of inverted U-shaped configuration having wire legs normally spaced substantially apart, the lower end portions of said legs merging smoothly with arcuate connecting segments of said frame extending circumferentially between and joining the adjacent legs of adjoining commissure supports, said U-shaped commissure supports and said connecting segments being formed integrally from the same piece of spring wire, each of said arcuate connecting segments having a major portion of the length thereof extending along a plane normal to the axis of said stent.

17. The stent of claim 16 in which each of the commissure supports of said frame is rounded at its upper end and the wire legs thereof are generally parallel along substantial portions of their length.

18. A flexible stent for supporting a valvular graft, said stent having an annular frame formed of spring wire, said frame including a triad of axially-projecting circumferentially-spaced commissure supports, each commissure support being of inverted U-shaped configuration having wire legs normally spaced apart at their lower end portions, said lower end portions of said legs merging smoothly with arcuate connecting segments of said frame extending circumferentially between and joining the adjacent legs of adjoining commissure supports, said U-shaped commissure supports and said connecting segments being formed integrally from the same piece of spring wire, and insert elements extending between said commissure supports, said insert elements being flexible and having upper margins disposed above said connecting segments of said frame.

19. The stent of claim 18 in which said insert elements are formed of flexible perforated sheet material.

20. The stent of claim 18 in which said insert elements are integral portions of a web of flexible perforated plastic material circumscribing said frame.

21. The stent of claim 18 in which said web is provided with scalloped upper edge portions between said commissure supports.

22. The stent of claim 18 in which the upper margins of said insert elements are arcuate.

23. The stent of claim 18 in which said insert elements extend from the upper margins thereof to the connecting portions of said frame.

24. The stent of claim 18 in which there is a sleeve of cloth between said frame and said insert elements, said cloth sleeve being stitched to said frame and said insert elements being stitched to said cloth sleeve.

25. The stent of claim 18 in which said insert elements are formed integrally from a sheet of flexible perforated polyglycol terephthalate.

26. The stent of claim 20 in which said web is formed from a material of sufficient flexibility that it does not significantly alter the ability of the spaced wire legs of each commissure support to flex towards and away from each other.

27. The stent of claim 20 in which said web is formed from polyglycol terephthalate.

28. A flexible stent for supporting a valvular graft, said stent having an annular frame formed of spring wire, said frame including a triad of axially-projecting circumferentially-spaced commissure supports, each commissure support being of inverted U-shaped configuration having wire legs normally spaced apart at their lower end portions, said lower end portions of said legs merging smoothly with arcuate connecting segments of said frame extending circumferentially between and joining the adjacent legs of adjoining commissure supports, said U-shaped commissure supports and said connecting segments being formed integrally from the same piece of spring wire, said wire of said frame having end portions joined together at a point intermediate the length of one of said arcuate connecting segments, said end portions being joined together by a tubular sleeve extending over and joined to both of said end portions.

29. The stent of claim 28, in which said sleeve is crimped tightly about both of said end portions.

* * * * *